United States Patent
Pilch et al.

(10) Patent No.: US 10,610,707 B2
(45) Date of Patent: Apr. 7, 2020

(54) ORAL CARE PRODUCT FOR SENSITIVE ENAMEL CARE

(75) Inventors: Shira Pilch, Highland Park, NJ (US); James Gerald Masters, Ringoes, NJ (US); Zhi Lu, Phillipsburg, NJ (US); Davide Miksa, Doylestown, PA (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/574,205

(22) PCT Filed: Jan. 28, 2011

(86) PCT No.: PCT/US2011/022867
§ 371 (c)(1),
(2), (4) Date: Jul. 19, 2012

(87) PCT Pub. No.: WO2011/094499
PCT Pub. Date: Aug. 4, 2011

(65) Prior Publication Data
US 2012/0288455 A1    Nov. 15, 2012

Related U.S. Application Data

(60) Provisional application No. 61/299,650, filed on Jan. 29, 2010.

(51) Int. Cl.
| | | |
|---|---|---|
| *A61K 8/19* | (2006.01) | |
| *A61K 8/25* | (2006.01) | |
| *A61Q 11/00* | (2006.01) | |
| *A61K 33/06* | (2006.01) | |
| *A61K 8/27* | (2006.01) | |
| *A61K 8/81* | (2006.01) | |

(52) U.S. Cl.
CPC .............. *A61Q 11/00* (2013.01); *A61K 8/19* (2013.01); *A61K 8/25* (2013.01); *A61K 8/27* (2013.01); *A61K 8/8164* (2013.01)

(58) Field of Classification Search
CPC ... A61K 8/19; A61K 8/27; A61K 8/25; A61K 8/8164; A61Q 11/00
See application file for complete search history.

(56) References Cited

U.S. PATENT DOCUMENTS

| | | |
|---|---|---|
| 3,538,230 A | 11/1970 | Pader et al. |
| 3,956,480 A | 5/1976 | Dichter et al. |
| 3,966,863 A | 6/1976 | Forward et al. |
| 3,980,767 A | 9/1976 | Chown et al. |
| 3,996,863 A | 12/1976 | Osborn |
| 4,110,083 A | 8/1978 | Benedict |
| 4,138,477 A | 2/1979 | Gaffar |
| 4,138,914 A | 2/1979 | Reeder |
| 4,198,394 A | 4/1980 | Faunce |
| 4,217,343 A | 8/1980 | Gaffar et al. |
| 4,314,990 A | 2/1982 | Denny, Jr. et al. |
| 4,328,205 A | 5/1982 | Taylor |
| 4,358,437 A | 11/1982 | Duke |
| 4,373,036 A | 2/1983 | Chang et al. |
| 4,485,090 A | 11/1984 | Chang |
| 4,521,551 A | 6/1985 | Chang et al. |
| 4,532,124 A | 7/1985 | Pearce |
| 4,634,589 A | 1/1987 | Scheller |
| 4,853,367 A | 8/1989 | Henzel et al. |
| 4,961,924 A * | 10/1990 | Suhonen .................. 424/52 |
| 4,992,258 A | 2/1991 | Mason |
| 5,015,467 A * | 5/1991 | Smitherman ............. 424/52 |
| 5,028,413 A | 7/1991 | Bianchi et al. |
| 5,032,178 A | 7/1991 | Cornell |
| 5,188,821 A | 2/1993 | Gaffar |
| 5,192,531 A | 3/1993 | Gaffar et al. |
| 5,240,697 A | 8/1993 | Norfleet et al. |
| 5,310,543 A | 5/1994 | Dawson |
| 5,334,375 A | 8/1994 | Nabi et al. |
| 5,352,439 A | 10/1994 | Norfleet et al. |
| 5,354,550 A | 10/1994 | Collins et al. |
| 5,356,615 A * | 10/1994 | Gaffar ........................ 424/49 |
| 5,505,933 A | 4/1996 | Norfleet et al. |
| 5,603,922 A | 2/1997 | Winston et al. |
| 5,605,677 A | 2/1997 | Schumann et al. |
| 5,624,652 A | 4/1997 | Aldcroft et al. |
| 5,645,853 A | 7/1997 | Winston et al. |
| 5,723,105 A | 3/1998 | Viscio et al. |
| 5,833,957 A | 11/1998 | Winston et al. |
| 5,843,406 A * | 12/1998 | Mordarski ............ A61K 8/24 424/49 |
| 5,876,701 A | 3/1999 | Wong et al. |

(Continued)

FOREIGN PATENT DOCUMENTS

| | | |
|---|---|---|
| EP | 0102200 | 3/1984 |
| EP | 0467548 | 1/1992 |

(Continued)

OTHER PUBLICATIONS

International Search Report and Written Opinion in International Application No. PCT/US2011/022867, dated Nov. 30, 2012.
Van Der Reijden et al., 1997, "Influence of polymers for use in saliva substitutes on de- and remineralization of enamel in vitro," Caries Research 31(3):216-223.
Acevedo et al., 2005, "The Inhibitory Effect of an Arginine Bicarbonate/Calcium Carbonate (CaviStat®)-Containing Dentifrice on the Development of Dental Caries in Venezuelan School Children," J. Clin. Dent. 16:63-70.
Amaechi et al., 2005, "Dental Erosion: Possible Approaches to Prevention and Control," J. Dentistry 33(3):243-252.
Anonymous, 2007, "Sensodyne Pronamel Toothpaste Sensodyne Enamel-Pro Toothpaste," Safeguarding Public Health, MHRA.
Ariely et al., 1966, "Synthesis of Poly-L-Arginine," Biopolymers 4(1):91-96.

(Continued)

*Primary Examiner* — Lezah Roberts

(57) ABSTRACT

Disclosed are anti-erosion oral care formulations and methods that provide erosion protection while maintaining adequate cleaning performance. The anti-erosion oral care formulations include a copolymer of a methylvinyl ether and a maleic anhydride and a metal compound or salt that becomes more soluble at acidic pH.

4 Claims, No Drawings

(56) References Cited

U.S. PATENT DOCUMENTS

| | | |
|---|---|---|
| 5,939,051 A | 8/1999 | Santalucia et al. |
| 6,036,944 A | 3/2000 | Winston et al. |
| 6,117,415 A | 9/2000 | Schwartz |
| 6,214,321 B1 | 4/2001 | Lee et al. |
| 6,217,851 B1 | 4/2001 | Kleinberg et al. |
| 6,241,972 B1 | 6/2001 | Herms et al. |
| 6,248,310 B1 | 6/2001 | Lee et al. |
| 6,294,163 B1 | 9/2001 | Dhal et al. |
| 6,447,578 B1 | 9/2002 | Ciccarelli |
| 6,447,756 B1 | 9/2002 | Dixit et al. |
| 6,447,758 B1 | 9/2002 | Carale et al. |
| 6,524,558 B2 | 2/2003 | Kleinberg et al. |
| 6,790,460 B2 | 9/2004 | Shefer et al. |
| 6,936,640 B2 | 8/2005 | McQueen et al. |
| 6,953,817 B2 | 10/2005 | Fisher et al. |
| 7,018,625 B2 | 3/2006 | Ulmer et al. |
| 7,402,416 B2 | 7/2008 | Szeles et al. |
| 7,435,409 B2 | 10/2008 | Nelson et al. |
| 2002/0037258 A1 | 3/2002 | Dodd et al. |
| 2003/0019162 A1 | 1/2003 | Huang |
| 2003/0026768 A1 | 2/2003 | Yu et al. |
| 2003/0072721 A1* | 4/2003 | Riley ............... A61K 8/19 424/49 |
| 2003/0165442 A1 | 9/2003 | Baig et al. |
| 2004/0126335 A1 | 7/2004 | Faller et al. |
| 2004/0241108 A1 | 12/2004 | Stanier et al. |
| 2005/0031553 A1 | 2/2005 | Mori et al. |
| 2005/0129628 A1 | 6/2005 | Stanier et al. |
| 2005/0175552 A1 | 8/2005 | Hoic et al. |
| 2005/0186288 A1 | 8/2005 | Chiou et al. |
| 2005/0196358 A1 | 9/2005 | Georgiades et al. |
| 2005/0281757 A1 | 12/2005 | Ibrahim et al. |
| 2006/0008423 A1 | 1/2006 | Araya et al. |
| 2006/0024246 A1 | 2/2006 | Maitra et al. |
| 2006/0039957 A1 | 2/2006 | Krumme |
| 2006/0045851 A1 | 3/2006 | Fitzgerald et al. |
| 2006/0251737 A1 | 11/2006 | Dutra Zanotto et al. |
| 2007/0014741 A1 | 1/2007 | Chiu |
| 2007/0025928 A1 | 2/2007 | Glandorf et al. |
| 2007/0053849 A1 | 3/2007 | Doyle et al. |
| 2007/0104660 A1 | 5/2007 | Miksa et al. |
| 2008/0044363 A1 | 2/2008 | Montgomery |
| 2008/0226566 A1 | 9/2008 | Poth et al. |
| 2008/0267891 A1 | 10/2008 | Zaidel et al. |
| 2008/0268001 A1 | 10/2008 | Zaidel et al. |
| 2009/0068259 A1 | 3/2009 | Pilch et al. |
| 2009/0202451 A1* | 8/2009 | Prencipe .......... A61K 8/25 424/49 |
| 2011/0059029 A1 | 3/2011 | Kohli et al. |

FOREIGN PATENT DOCUMENTS

| | | |
|---|---|---|
| EP | 0480812 | 4/1992 |
| EP | 0845976 | 6/1998 |
| EP | 1260482 | 11/2002 |
| EP | 1508324 | 2/2005 |
| EP | 1886664 | 2/2008 |
| GB | 1598233 | 9/1981 |
| JP | H06-065083 | 3/1994 |
| JP | H09-002926 | 1/1997 |
| JP | H09-295924 | 11/1997 |
| JP | 2001-247310 A | 12/2001 |
| JP | 2002-316920 | 10/2002 |
| JP | 2009-515905 | 4/2009 |
| JP | 2012-528172 | 11/2012 |
| RU | 2085184 | 7/1997 |
| TW | 201201852 | 1/2012 |
| WO | WO 93/007851 | 4/1993 |
| WO | WO 00/016712 | 3/2000 |
| WO | WO 01/070178 | 9/2001 |
| WO | WO 02/045678 | 6/2002 |
| WO | WO 04/032674 | 4/2004 |
| WO | WO 04/047784 | 6/2004 |
| WO | WO 05/063185 | 7/2005 |
| WO | WO 07/051546 | 5/2007 |
| WO | WO 07/076444 | 7/2007 |
| WO | WO 08/041055 | 4/2008 |
| WO | WO 08/122578 | 10/2008 |
| WO | WO 09/009814 | 1/2009 |
| WO | WO 09/032404 | 3/2009 |
| WO | WO 09/074589 | 6/2009 |
| WO | WO 2009/099454 | 8/2009 |
| WO | WO 10/054494 | 5/2010 |
| WO | WO 11/084673 | 7/2011 |
| WO | WO 11/094505 | 8/2011 |

OTHER PUBLICATIONS

Cunin et al., 1986, "Biosynthesis and Metabolism of Arginine in Bacteria," Microbiological Reviews, 50(3):314-352.

Hefferren, 1976, "A Laboratory Method for Assessment of Dentifrice Abrasivity," J. Dent. Res. 55(4):563-573.

International Search Report and Written Opinion in International Application No. PCT/US08/061925, dated Feb. 5, 2010.

International Search Report and Written Opinion in International Application No. PCT/US09/044349, dated Dec. 8, 2009.

International Search Report and Written Opinion in International Application No. PCT/US10/021582, dated Aug. 9, 2011.

International Sarch Report and Written Opinion in International Application No. PCT/US10/060970, dated May 31, 2012.

Jal et al., 2004, "Chemical modification of silica surface by immobilization of functional groups for extractive concentration of metal ions," Talanta 62(5):1005-1028.

Johnson et al., 2006, "Oral Health and General Health," Advances in Dental Research 19:118-121.

McConnell et al., 2010, "Bacterial plaque retention on oral hard materials: Effect of surface roughness, surface composition, and physisorbed polycarboxylate," J. Biomedical Materials Research Part A 92(4):1518-1527.

Pashley et al., 1984, "Effects of Desensitizing Dentifrices in vitro," J. Periodontology 55(9):522-525.

Pashley et al., 1993, "The Effects of Outward Forced Convective Flow on Inward Diffusion in Human Dentine in vitro," Arch. Oral Biol. 38(7):577-582.

Pashley et al., 2002, "The Effects of Outward Forced Convective Flow on Inward Diffusion of Potassium across Human Dentin," American J. of Dentistry, Medline Database Accession No. NLM12572645, Abstract.

Sakai et al., 2003, "Anion-Mediated Transfer of Polyarginine Across Liquid and Bilayer Membranes," J. Am. Chem. Soc. 125(47):14348-14356.

Stober et al., 1968, "Controlled Growth of Monodisperse Silica Spheres in the Micron Size Range," J. Colloid and Interface Science 26:62-69.

Zhang et al., 1998, "The Effects of Pain-Free Desensitizer on Dentine Permability and Tubule Occlusion over Time, in vitro," J. Clinical Periodontology 25(11 Pt. 1):884-891.

Van Der Reijden W A, et al., XP002128236—Influence of Polymers for Use in Saliva Substitutes on DE and Remineralization of Enamel in vitro, vol. 31, pp. 216-223.

* cited by examiner

ORAL CARE PRODUCT FOR SENSITIVE ENAMEL CARE

CROSS REFERENCE TO RELATED APPLICATION

This application is a national stage entry under 35 U.S.C. § 371 of International Patent Application No. PCT/US2011/022867, filed on Jan. 28, 2011, which claims priority to U.S. Provisional Patent Application No. 61/299,650, filed on Jan. 29, 2010, which are incorporated herein by reference.

FIELD OF THE INVENTION

This invention relates to anti-erosion oral care compositions that provide erosion protection while maintaining adequate cleaning performance

BACKGROUND OF THE INVENTION

The erosion of dental enamel can lead to pain, discoloration, mechanical failure, and greater susceptibility to dental carries. Chemical erosion of tooth enamel may arise from the presence of acid in the oral cavity. Saliva constituents, mainly proteins and minerals, along with the pellicle are integral in protecting against an erosive challenge. The minerals and proteins in saliva help provide a chemical barrier to slow down or shift the complex dynamic equilibria of hard tissue demineralization, while the pellicle will provide a diffusion barrier to accomplish the same process.

An oral care composition may protect teeth in a variety of ways. Many oral care compositions are designed to increase the pH in the oral cavity. A common strategy when attempting to control oral pH is to include an alkaline agent in the formulation of the oral care composition. The alkaline agent reacts with acid to neutralize the acid, forming water and a salt. This process raises the pH in the oral cavity. However, even when the pH in the oral cavity is high, the pH at the surface of the teeth, where cariogenic bacteria may be present, may be locally lower than the oral cavity in general due to bacterial activity. Soluble bases are not able to preferentially locate at the tooth surface, where acid does the most damage to teeth.

Metal ions are able to protect teeth from erosion. Certain metal ions can react with the surface of the enamel to shift the solubility equilibrium away from dissolution of the tooth's enamel. Some examples of ions that have been investigated for this purpose are calcium, zinc, tin, aluminum, strontium and others. Phosphate salts of these metals have been particularly interesting due to the high phosphate content in dental enamel.

Insoluble or slightly soluble metal compounds have been investigated as metal ion sources for tooth remineralization. By combining insoluble metal compounds with polymers, the insoluble compounds become more easily dispersed in the oral care composition. Additionally, the polymers may improve the residence time of the metal agent in the oral cavity. However, the main benefit of having a source of metal ions would be achieved at the surface of the tooth. Accordingly, there is a need for a long lasting oral care composition that can deliver metal containing compounds to and control pH at the surface of the tooth to prevent dental erosion.

SUMMARY OF THE INVENTION

In accordance with a feature of an embodiment, there is provided a composition and method for the prevention of dental erosion comprising an oral care composition that includes an orally acceptable vehicle, a copolymer of a methylvinyl ether and a maleic anhydride, a metal compound or salt that becomes more soluble at acidic pH, and an abrasive. While not wishing to be bound by any theory of operation, it is believed that application of the composition to the teeth protects tooth enamel from erosion by forming a barrier of polymer and metal compound at the surface of a tooth. The metal compound is eroded by acids, which substitutes for erosion that otherwise could occur at the tooth. In addition to helping spatially locate the metal compound at the tooth surface, the inventors believe that the copolymer of methylvinyl ether and maleic anhydride may also reduce bacterial adhesion at the surface of the tooth.

In accordance with an additional embodiment, the invention includes a method of reducing acid based erosion of teeth comprising administering an oral care composition comprised of an orally acceptable vehicle, a copolymer of a methylvinyl ether and a maleic anhydride, a metal compound or salt that becomes more soluble at acidic pH, and an abrasive, and optionally applying a shear stress to the composition to shear-align a layer of the copolymer and metal compound to make the layer more homogeneous. When the composition is applied using a shear stress, enhanced erosion protection is derived from the additional homogeneity of the composition.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

The headings (such as "Background" and "Summary,") used herein are intended only for general organization of topics within the disclosure of the invention, and are not intended to limit the disclosure of the invention or any aspect thereof. In particular, subject matter disclosed in the "Background" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. All references cited in the Description section of this specification are hereby incorporated by reference in their entirety.

The description and specific examples, while indicating embodiments of the invention, are intended for purposes of illustration only and are not intended to limit the scope of the invention. Recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated to recite activities that have been done (i.e., using the past tense), are not intended to be a representation that given embodiments of this invention have, or have not, been performed.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. As used herein, the word "include," and its variants, is intended to be non-limiting, such that recitation of items in a list is not to the exclusion of other like items that may also be useful in the materials, compositions, devices, and methods of this invention. In a similar manner, the description of certain advantages or disadvantages of known materials and methods is not intended to limit the scope of the embodiments to their exclusion. Indeed, certain embodiments may include one or more known materials or methods, without suffering from the disadvantages discussed herein.

As used herein, the term "comprising" means that other steps and other components that do not affect the end result may be utilized. The term "comprising" encompasses the expressions "consisting of," and "consisting essentially of." The expression "effective amount," as used herein denotes an amount of a compound or composition sufficient to significantly induce a positive benefit, preferably an oral health benefit, but low enough to avoid serious side effects, i.e., to provide a reasonable benefit to risk ratio, within the sound judgment of a person having ordinary skill in the art. The use of singular identifiers such as "the," "a," or "an" is not intended to be limiting solely to the use of a single component, but may include multiple components.

The expressions "carrier" or "aqueous carrier" as used throughout this description denote any safe and effective materials for use herein. Such materials include, for example, thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

All percentages and ratios used herein are by weight of the oral care composition, unless otherwise specified. All measurements are made at 25° C., unless otherwise specified.

Throughout this description and claims, the disclosure of a certain numerical value (e.g., temperature, weight percent of components, etc.) is meant to denote that value, plus or minus an additional value that would be understood by persons having ordinary skill in the art, depending on the variable and the degree of measurement error typically associated with that value. For example, a given temperature would be understood by a person having ordinary skill in the art to include up to 10% variability, given the instrument used to measure the temperature.

The dentifrice of the present invention combines copolymer of methylvinyl ether and maleic anhydride, a copolymer having enhanced mucoadhesive properties, with an insoluble or slightly soluble metal compound to form compositions that are useful for combating acid erosion of dental enamel. A particularly preferred copolymer of methylvinyl ether and maleic anhydride is GANTREZ®, a well known commercially available copolymer, or GANTREZ® AN, a copolymer of polymethyl vinyl ether and maleic anhydride (PVM/MA). The Gantrez polymers are commercially available from ISP Technologies, Inc., Bound Brook, N.J. 08805. Gantrez polymers have been known and used in oral care preparations, and are described, inter alia, in U.S. Pat. Nos. 4,521,551, 4,373,036, and 4,485,090, the disclosures of each of which are incorporated by reference herein in their entirety.

While not intending on being bound by any theory of operation, the inventors believe that the Gantrez polymer, when used in the compositions and methods described herein, prevents the adherence of carriogenic bacteria to the enamel, has a long residence time at the enamel surface. It also is believed that the Gantrez polymer spatially confines some of the metal compound to the surface of the tooth. As the local environment around the tooth becomes acidic, the metal compound is believed to become more soluble. The inventors believe that the process of solubilizing the metal compound both neutralizes acid and provides beneficial soluble metal ions. The long residence time of the Gantrez at the enamel surface is believed to provide a longer residence time for the metal compounds.

The compositions and methods of use of the present invention also provide enhanced acid protection by forming more ordered surface films when subjected to shear stress. Shear stress originating from acts such as brushing, scrubbing, rubbing with a finger, and the like, results in shear alignment of the composition. The term "shear alignment" as used in the specification and claims refers to a process in which a material becomes, at least partially, more ordered in response to an applied shear stress. Shear alignment will be understood to create a more homogeneous composition as a result of at least partial ordering. In the present invention, improved ordering may occur due to the formation of a more regular array of polymer, a more regular array of metal in the polymer, or a combination of both more ordered polymer and metal.

To prepare an anti-erosion oral care composition of the present invention the copolymer of a methylvinyl ether and a maleic anhydride (Gantrez), a metal compound or salt that becomes more soluble at acidic pH, and an abrasive are incorporated into an orally acceptable vehicle.

The oral care compositions of the various embodiments preferably are in the form of a dentifrice. The term "dentifrice" as used throughout this description, denotes a paste, gel, or liquid formulation. The dentifrice may be in any desired form, such as toothpaste; (including deep striped, surface striped, multi-layered, having a gel surround the paste); powder; beads; mouthwash; mouth rinses; lozenge; dental gel; a periodontal gel; a liquid suitable for painting a dental surface; a chewing gum; a dissolvable, partially dissolvable or non-dissolvable film or strip; a wafer; a wipe or towelette; an implant; a foam; a troche; a dental floss or any combinations thereof. Preferably, the dentifrice is a toothpaste.

The expression "orally acceptable vehicle" used in the context of the present invention means any vehicle useful in formulating any of the dentifrices described above. Suitable orally acceptable vehicles include, for example, one or more of the following: a solvent; an alkaline agent; a humectant; a thickener; a surfactant; an abrasive; an anti-calculus agent; a colorant; a flavoring agent; a dye; a potassium containing salt; an anti-bacterial agent; desensitizing agents; stain reducing agents; and mixtures thereof.

The term "mucoadhesive polymer" as used in the specification and claims includes within its meaning hydrophilic polymers and hydrogels. Some polymers useful in the practice of the current invention include: cellulose derivatives; polyvinylpyrrolidones; polyacrylates; polyethers; polyanhydrides; polysaccharides; polyvinylphosphates; and copolymers incorporating these functionalities.

A preferable class of mucoadhesive polymers are the polycarboxylates. The term polycarboxylate means oligomers or polymers with repeat units that have carboxylate functional groups. A non-limiting example of the most preferable polycarboxylate mucoadhesive is a copolymer of a methylvinyl ether and a maleic anhydride, known commercially as Gantrez. Gantrez is advantageous due to its long residence time at enamel surfaces and its ability to deter bacterial adhesion to enamel. Used in combination with an insoluble or slightly soluble metal compound, Gantrez may place a source of metal ions in spatial proximity to the tooth while maintaining a longer residence time of the metal compound in proximity to the tooth.

A mucoadhesive polymer such as a polycarboxylate may be incorporated into the orally acceptable vehicle of the present invention in amounts in the range of 0.01 to 20% by weight, preferably 0.1 to 10% by weight and most preferably at 0.5 to 7% by weight of the component. Mixtures of the mucoadhesive polymers may also be used. Gantrez is the preferred mucoadhesive polymer.

The expression "metal compound or salt" as used in the specification and claims includes within its meaning salts and compounds of calcium and zinc. These salts and compounds include, calcium carbonate, aragonite, zinc oxide, zinc carbonate, zinc citrate, zinc silicate, zinc stannate, zinc benzoate, zinc tetrafluoroborate, zinc hexafluorosilicate and other calcium or zinc compounds, preferably calcium carbonate or zinc oxide, most preferably calcium carbonate.

Some insoluble or slightly soluble metal compounds have the ability to react with acid to form metal ions in solution. Calcium carbonate is an example of a metal compound that may react with acid to form calcium ions in solution:

$$CaCO_3 + 2HCl \rightarrow Ca^{2+} + 2Cl^- + CO_2 + H_2O$$

This reaction consumes acid to yield a soluble calcium salt, water and carbon dioxide. The pH of calcium carbonate is approximately 8.75. Another example of a metal compound that consumes acid to provide soluble metal ions is zinc oxide. Zinc oxide has the ability to react with acid to four zinc ions in solution:

$$ZnO + HCl \rightarrow Zn^{2+} + 2Cl^- + H_2O$$

This reaction consumes acid to yield a zinc salt and water. The pH of ZnO is approximately 6.95, which indicates that in an environment that is more acidic (lower pH) than 6.95, the ZnO will dissolve, consuming acid and raising the pH.

The term "insoluble or slightly soluble" as used in the specification and claims refers to the solubility of the metal salts and compounds. pH may affect the solubility of compounds which may make these compounds more or less soluble at different pH. Solubility encompasses a dynamic equilibrium between precipitation and dissolution which may be affected by factors including but not limited to the presence of soluble chelating agents or acids. Insoluble or slightly soluble can be understood to mean compounds which are less than 1% soluble by weight in pH 7 water. At lower or higher pH, the compounds may become significantly more soluble, and that the phrase "a metal compound or salt which becomes more soluble at acidic pH" will refer to an insoluble or slightly soluble compound that may become more soluble upon lowering of the local pH, preferably calcium carbonate or zinc oxide, most preferably zinc oxide.

Abrasives may be incorporated in the orally acceptable vehicle of the present invention and preferred abrasives are siliceous materials, such as silica. A preferred silica is a precipitated amorphous hydrated silica, such as Sorbosil AC-35, marketed by Crosfield Chemicals, or Zeodent 115 from Huber Company but other abrasives may also be employed, including hydroxyapatite, sodiummetaphosphate, potassium metaphosphate, tricalcium phosphate, calcium phosphate dihydrate, anhydrous dicalciumphosphate, calcium pyrophosphate, magnesium orthophosphate, trimagnesium phosphate, calcium carbonate, sodium bicarbonate, alumina trihydrate, aluminum silicate, calcined alumina, titania, and bentonite. The concentration of abrasive in the toothpaste compositions of the present invention will normally be in the range of 5 to 40% by weight and preferably 10 to 25% by weight.

An alkaline agent such as an alkali metal compound including sodium hydroxide, potassium hydroxide, sodium bicarbonate, sodium carbonate, N-sodium silicate (a 3.22 weight ratio of sodium silicate in 34.6% water available from PQ Corporation) may be incorporated in the orally acceptable vehicle of the present invention in amounts in the range of 0.5 to 15% by weight, preferably 1 to 8% by weight and most preferably at 1 to 5% by weight of the component. Mixtures of the above alkali metal compounds may also be used. Sodium hydroxide is the preferred alkaline agent.

A humectant used in the preparation of the orally acceptable vehicle may be a mixture of humectants, such as glycerol, sorbitol and a polyethylene glycol of molecular weight in the range of 200 to 1000, but other mixtures of humectants and single humectants may also be employed. The humectant content is in the range of 10 to 50% by weight and preferably 20 to 40% by weight of the dentifrice component. The water content is in the range of 20 to 50% by weight and preferably 30 to 40% by weight.

Thickeners used in the preparation of the orally acceptable vehicle include organic and inorganic thickeners. Inorganic thickeners which may be included in the orally acceptable vehicle include amorphous silicas. An inorganic thickener may be incorporated in the orally acceptable vehicle of the present invention at a concentration of 0.5 to 5% by weight and preferably 1 to 3% by weight.

Organic thickeners of natural and synthetic gums and colloids may also be used to prepare the orally acceptable vehicle of the present invention. Examples of such thickeners are carrageenan (Irish moss), xanthan gum, sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose. An organic thickener may be incorporated in the orally acceptable vehicle of the present invention at a concentration of 0.1 to 3% by weight and preferably 0.4 to 1.5% by weight.

Surfactants may be incorporated in the orally acceptable vehicle to provide foaming properties. The surfactant is preferably anionic or nonionic in nature. Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate. The surfactant agent may generally be present in the orally acceptable vehicle compositions of the present invention at a concentration of 0.5 to 10% by weight and preferably 1.0 to 5.0% by weight.

The source of desensitizing potassium ion may generally be a water soluble potassium salt including potassium nitrate, potassium citrate, potassium chloride, potassium bicarbonate and potassium oxalate with potassium nitrate being preferred. The potassium salt is generally incorporated in one or more of the dentifrice components at a concentration of 1 to about 20% by weight and preferably 3 to 10% by weight.

Pyrophosphate salts having anticalculus efficacy useful in the practice of the present invention include water soluble salts such as dialkali or tetraalkali metal pyrophosphate salts such as $Na_4P_2O_7$ (TSPP), $K_4P_2O_7$, $Na_2P_2O_7$, $Na_2H_2P_2O_7$ and $K_2H_2P_2O_7$. Polyphosphate salts include the water soluble alkali metal tripolyphosphates such as sodium tripolyphosphate and potassium tripolyphosphate. The pyrophosphate salts are incorporated in the dentifrice composition of the present invention at a concentration of 0.5 to 2% by weight, and preferably 1.5 to 2% by weight and the polyphosphate salts are incorporated in the dentifrice composition of the present invention at a concentration of 1 to 7% by weight.

Colorants such as pigments and dyes may be used in the practice of the present invention. Pigments include nontoxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C #Yellow 15 lake. The pigments have a particle size in the range of 5-1000 microns, preferably 250-500 microns, and are present at a concentration of 0.5 to 3% by weight.

Dyes used in the practice of the present invention are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium slat of 4-{[4-(N-ethyl-p-sulffobenzyno)-phenyl]-(4-hydroxy-2-sulfoniumphenyl)mewthylene}-[1-(N-ethyl-N-p-sulfobenzyl)-G)-3,5cyclohexadienimine], FD&C Blue No. 1 (disodium salt of dibenzyldiethyldiaminotriphenylcarbinol trisulfonic acid of indigo tin) and mixtures thereof in various proportions. The concentration of the dye for the most effective result in the present invention is present in the dentifrice composition in an amount from 0.0005 percent to 2 percent of the total weight.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon lemon, and orange, and methyl salicylate. Suitable sweetening agents include sucrose, lactose, maltose, sorbitol, xylitol, sodium cyclamate, perillatine, and sodium saccharin. Suitably, flavor and sweetening agents may together comprise from 0.0005% to 2 or more of the preparations.

Antibacterial agents are non-cationic antibacterial agents based on phenolic and bisphenolic compounds, halogenated diphenyl ethers such as Triclosan, benzoate esters and carbanilides as well as cationic antibacterial agents such as chlorhexidine digluconate. Such antibacterial agents can be present in quantities of from 0.03 to 1% by weight of the particular component.

When noncationic antibacterial agents or antibacterial agents are included in any of the dentifrice components, there is also preferably included from 0.05 to 5% of an agent which enhances the delivery and retention of the agents to, and retention thereof on oral surfaces. Such agents useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez. e.g. AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0.05 to 3% by weight.

To prepare the dentifrice components of the present invention, generally the humectants, for example, propylene glycol, polyethylene glycol ingredients, are dispersed with any organic thickeners, sweetener, pigments such as titanium dioxide and any polyphosphates included as anticalculus ingredients. Water is then added into this dispersion along with any antibacterial agent such as Triclosan, any antibacterial enhancing agent such as Gantrez and any anticalculus additional agents. The mucoadhesive polymer and metal compound or salt which becomes more soluble at acidic pH is then mixed into the dispersion. These ingredients are mixed until a homogenous phase is obtained. Thereafter inorganic thickener, silica abrasive, flavor and surfactant ingredients are added and the ingredients mixed at high speed under vacuum of from about 20 to 100 mm of Hg. The resultant product is a homogeneous, semi-solid, extrudable paste product.

The preparation of dentifrice compositions is well known in the art. U.S. Pat. Nos. 3,996,863, 3,980,767, 4,328,205, and 4,358,437, which are incorporated herein by reference, describe toothpastes and methods of production thereof which may be utilized for the production of the dentifrices according to the present invention.

SPECIFIC EMBODIMENTS OF THE INVENTION

The invention is further described in the following examples. The examples are merely illustrative and do not in any way limit the scope of the invention as described and claimed.

EXAMPLE 1

Sintered HAP, human enamel, polished enamel, and silicon were soaked in ethanol for 30 min and then dried in a stream of nitrogen. Whole human saliva was centrifuged for 10 min at 12,900 g at 4° C., yielding a supernatant of clarified saliva. The samples were then immersed in the clarified saliva for 1 h at 37° C. to form a pellicle on the surface. After pellicle formation, the substrates were rinsed in deionized ultrafiltered (DIUF) water for 30 s to remove any loosely bound proteins. The samples then were placed directly into whole human saliva for 30 min, 3 h, or 24 h at 37° C. An identical batch of pellicle-coated samples were treated with either a 0.8 wt % aqueous solution of neutralized Gantrez or a 0.05 wt % aqueous solution of neutralized Carbopol for 5 min, followed by a 30-s rinse with DIUF water to remove unbound polymer, before being placed in whole saliva. Whole human saliva was collected fresh, from a single source. All data were collected from studies conducted using the same batch of saliva. Each set of HAP, enamel, and polished enamel samples (untreated, Gantrez, and Carbopol) were immersed in 10 mL of the whole human saliva. The substrates were shaken throughout each given time period to promote bacterial growth. Once the samples were removed from the whole saliva, the bacteria were fixed onto the samples' surfaces by placing them in 10, 20, 40, 60, 80, and 100% ethanol for 10 min each. The samples were then allowed to air dry. Scanning Electron Microscopy was used to measure the bacterial coverage on the surfaces.

Table 1 shows the bacterial coverage of polished enamel, enamel, and sintered hydroxyapatite after incubation with human saliva and exposure to different mucoadhesive polymers. On enamel (En), both Carbopol and Gantrez show lower bacterial coverage compared to a native enamel sample with no mucoadhesive. The Gantrez treated surface demonstrates lower bacterial coverage over the course of the experiment when compared to the Carbopol treated surface, which shows that Gantrez may provide longer protection against bacterial attack at the tooth surface. For the polished enamel surface (P-En), both Gantrez and Carbopol demonstrate lower bacterial coverage than the native surface. The Carbopol treated polished enamel surface shows lower bacterial coverage at three hours, but Gantrez has much lower bacterial coverage at the 24 hour mark when compared to the Carbopol samples. The Gantrez treated polished enamel surface demonstrates the ability to inhibit bacterial coverage more effectively over longer time scales.

TABLE 1

Bacterial Coverage

| | | Bacterial Coverage (%) | | |
|---|---|---|---|---|
| Surface Type | | 30 minutes | 3 hours | 24 hours |
| Native | P-En | 2.5 | 2.6 | 11.0 |
| | En | 0.5 | 5.0 | 45 |
| | HAP | 2.7 | 7.5 | 12.0 |
| Carbopol | P-En | 0 | 0.2 | 2.7 |
| | En | 0.1 | 2.5 | 5.0 |
| | HAP | 0.1 | 3.0 | 3.3 |
| Gantrez | P-En | 0 | 1.0 | 1.1 |
| | En | 0.1 | 2.5 | 2.7 |
| | HAP | 1.0 | 5.0 | 7.7 |

EXAMPLE 2

An anti-erosion toothpaste was prepared in which the mucoadhesive polymer was Gantrez, the metal compound was precipitated calcium carbonate, and high cleaning silica was used as an abrasive. Table 2 contains the ingredients of this anti-erosion toothpaste composition.

TABLE 2

Low Polymer Formulation

| Ingredient | Weight % |
|---|---|
| Water | q.s. |
| Glycerin | 45 |
| Sodium Monofluorophosphate | 0.76 |
| Sodium Hydroxide (50%) | 1 |
| Sodium Lauryl Sulfate | 1.15 |
| High Cleaning Silica Zeo105 | 6.5 |
| Amorphous Silica | 5 |
| Precipitated Calcium Carbonate | 14.8 |
| Sodium CMC | 0.4 |
| Xanthan Gum | 0.1 |
| Carbopol | 0.1 |
| Gantrez | 0.5 |
| Flavor | 1.1 |

EXAMPLE 3

A anti-erosion toothpaste was prepared in which the mucoadhesive polymer was Gantrez, the metal compound was precipitated calcium carbonate, and high cleaning silica was used as an abrasive. Table 3 contains the ingredients of this anti-erosion toothpaste composition.

TABLE 3

High Polymer Formulation 1

| Ingredient | Weight % |
|---|---|
| Water | q.s. |
| Glycerin | 45 |
| Sodium Monofluorophosphate | 0.76 |
| Sodium Hydroxide (50%) | 1 |
| Sodium Lauryl Sulfate | 1.15 |
| High Cleaning Silica Zeo105 | 6.5 |
| Amorphous Silica | 5 |
| Precipitated Calcium Carbonate | 14.8 |
| Sodium CMC | 0.4 |
| Xanthan Gum | 0.2 |
| Carbopol | 0.2 |
| Gantrez | 2.0 |
| Flavor | 1.1 |

EXAMPLE 4

A anti-erosion toothpaste was prepared in which the mucoadhesive polymer was polyvinylphosphonic acid (32.5%), the metal compound was precipitated calcium carbonate, and high cleaning silica was used as an abrasive. Table 4 contains the ingredients of this anti-erosion toothpaste composition.

TABLE 4

High Polymer Formulation 2

| Ingredient | Weight % |
|---|---|
| Water | q.s. |
| Glycerin | 45 |
| Sodium Monofluorophosphate | 0.76 |
| Sodium Hydroxide (50%) | 1 |
| Sodium Lauryl Sulfate | 1.15 |
| High Cleaning Silica Zeo105 | 6.5 |
| Amorphous Silica | 5 |
| Precipitated Calcium Carbonate | 14.8 |
| Sodium CMC | 0.4 |
| Xanthan Gum | 0.1 |
| Carbopol | 0.1 |
| Polyvinylphosphonic Acid (32.5%) | 6.0 |
| Flavor | 1.1 |

Anti-erosion evaluations were conducted to demonstrate the benefits of the anti-erosion toothpaste composition when subject to an acid challenge test. In the acid challenge test, polished enamel surfaces were treated with 5% citric acid for 30 seconds to create damaged tooth surfaces. The acid etched enamel surfaces were then exposed to a regimen for 4 days which consisted of the samples being soaked in a toothpaste slurry (1:1 toothpase:water) for 1 minute in both the morning and the evening. In between the two slurry soaks, four 2 minute acid challenges were introduced using surrogate orange juice (1% citric acid, pH=3.8). The enamel loss was then measured by profilometry. A commercial anti-erosion toothpaste that did not contain a Gantrez polymer (containing fluoride) was used as the benchmark.

The enamel samples from the two anti-erosion toothpaste compositions in the acid challenge test show significantly less enamel loss (0.06 microns for the Gantrez sample and 0.09 microns for the polyvinylphosphonic acid vs. 0.24 for the benchmark) than the benchmark, indicating the compositions of this invention provide enhanced protection against tooth erosion.

What is claimed is:

1. An oral care composition comprising:
   (a) an orally acceptable vehicle;
   (b) 0.05-3% by weight of a mucoadhesive polymer, wherein said mucoadhesive polymer is a copolymer of a methylvinyl ether and a maleic anhydride;
   (c) a calcium compound or salt that becomes more soluble at acidic pH in an effective amount to provide protection against erosion of tooth enamel; and
   (d) 5-40% by weight of a siliceous abrasive,
   wherein the calcium compound or salt is precipitated calcium carbonate having a pH of about 8.75, which, when solubilized, reacts with the tooth enamel to shift the solubility equilibrium away from dissolution of the tooth enamel, wherein the mucoadhesive polymer confines some of the calcium compound or salt at the surface of a tooth, wherein the calcium compound or salt has a longer residence time in proximity to the tooth, where the residence time is longer compared to a composition which does not contain the mucoadhesive polymer, and
   wherein the composition does not include triclosan; and
   wherein the composition has less enamel loss, when measured against a reference standard, upon challenge in an aqueous solution with about 5% by wt. of citric acid.

2. A method of reducing acid based erosion of teeth comprising:
   1) providing an effective amount of the oral care composition of claim 1; and
   2) delivering the composition to the oral cavity of a subject, wherein delivering the composition deposits a layer of the copolymer of a methylvinyl ether and a maleic anhydride and metal compound or salt on tooth enamel.

3. The oral care composition of claim 1, wherein the composition comprises more precipitated calcium carbonate than siliceous abrasive.

4. The oral care composition of claim 1, wherein the composition is in the form of a single homogeneous phase.

* * * * *